United States Patent [19]

Brown et al.

[11] Patent Number: 5,311,878
[45] Date of Patent: May 17, 1994

[54] REAL-TIME ELECTRICAL IMPEDANCE TOMOGRAPHY SYSTEM

[75] Inventors: Brian H. Brown; David C. Barber, both of Sheffield, England

[73] Assignee: British Technology Group Limited, London, England

[21] Appl. No.: 952,493
[22] PCT Filed: Jun. 7, 1991
[86] PCT No.: PCT/GB91/00915
  § 371 Date: Dec. 8, 1992
  § 102(e) Date: Dec. 8, 1992
[87] PCT Pub. No.: WO91/19454
  PCT Pub. Date: Dec. 25, 1991

[30] Foreign Application Priority Data

Jun. 13, 1990 [GB] United Kingdom ............... 9013177

[51] Int. Cl.$^5$ .............................................. A61B 5/05
[52] U.S. Cl. ................................................ 128/734
[58] Field of Search ................... 128/734; 364/413.13

[56] References Cited

U.S. PATENT DOCUMENTS

| 4,486,835 | 12/1984 | Bai et al. ............................ 128/734 |
| 4,539,640 | 9/1985 | Fry et al. . |
| 4,617,939 | 10/1986 | Brown et al. ......................... 128/734 |
| 4,649,932 | 3/1987 | Smith . |
| 4,920,480 | 4/1990 | Isaacson ............................. 128/734 |
| 5,184,624 | 2/1993 | Brown et al. ........................ 128/734 |

FOREIGN PATENT DOCUMENTS 0085490 8/1983 European Pat. Off. .
2138148 10/1984 United Kingdom .

OTHER PUBLICATIONS

IEEE Engineering in Medicine and Biology Magazine, vol. 8, No. 1, Mar. 1989, New York US pp. 39–45; B. M. Eyuboglu et al.

Medical Physics, vol. 16, No. 2; D. C. Barber: "A review of image reconstruction techniques for electrical impedance tomography".

Primary Examiner—Ruth S. Smith
Attorney, Agent, or Firm—Cushman, Darby & Cushman

[57] ABSTRACT

A method of, and apparatus for, real-time imaging are described employing a plurality of contact electrodes (1) located for example around the thorax (2) with simultaneous measurement of potential between adjacent pairs of electrodes (1), digital demodulation of the potentials, and measurement and division of the drive current into the potential measurements before image reconstruction by the use of transputers (20, 22, 24 and 26).

6 Claims, 2 Drawing Sheets

REAL-TIME ELECTRICAL IMPEDANCE TOMOGRAPHY SYSTEM

BACKGROUND OF THE INVENTION

This invention relates to a real-time electrical impedance tomography (EIT) system to provide for example blood flow imaging.

Tomography systems are described in GB-PS 2 119 520B or GB-PS 2 160 323B (U.S. Pat. No. 4,617,939 corresponding to both the content of the U.S. patent being incorporated hereinto by reference) or WO 89/09564 on which the present applicants/inventors are named as inventors, and in which the impedance imaging system consists of a data collection system (the data being measured potentials between pairs of electrodes in a series of contact electrodes attached around a human or animal body, and in which another pair is a "drive" pair between which currents are caused to flow) and an image reconstruction system. Frames of data could be collected serially by the data collection system at twenty-four frames per second but image construction could only be carried out at approximately one frame per second. Whilst this is not a disadvantage in extracting certain slowly changing physiological data there are other data requirements where it is necessary to produce images much more quickly—for example, when observing blood flow in the body during the cardiac cycle.

In order to produce a system able to produce images much more quickly two developments are required. Firstly, a much faster digital processor or computer in order to implement the image construction algorithm rapidly. Secondly, the data collected from the human body has to be improved in quality and in particular the noise level reduced. In the previous system noise level could be reduced by averaging signals over several seconds before constructing an image. However, averaging is not possible in a system running rapidly in real-time and therefore the noise level must be reduced by other means.

SUMMARY OF THE INVENTION

According to a first aspect of the present invention, there is provided a method of real time imaging using electrical impedance tomography, comprising:
a) arranging a plurality of pairs of surface electrodes at spaced apart locations around a body to be investigated;
b) applying constant current drive to selected electrodes;
c) measuring the resulting potentials between adjacent pairs of other electrodes; and
d) forming images using an algorithm implemented as a single matrix multiplication of the measured data set with a matrix of weights, whereby the measurement noise is minimised by;
  (i) measuring the potentials between adjacent pairs of said other electrodes simultaneously;
  (ii) de-modulating the potential measurement by digital signal processing, and
  (iii) measuring the drive current at the same time as the potentials, and dividing the drive current into potential measurements before image reconstruction.

According to a second aspect of the invention there is provided apparatus for carrying out the method defined above, comprising:
a) a plurality of pairs of contact electrodes;
b) means to apply constant current drive to selective electrodes;
c) means to measure the resulting potentials between adjacent pairs of other electrodes;
d) means to form images using an algorithm implemented as a single matrix multiplication of the measured data set with a matrix of weights wherein there is further provided:
  (i) means to measure the potentials between adjacent pairs of said other electrodes simultaneously;
  (ii) digital signal processing means to demodulate the potential measurement; and
  (iii) means to measure the drive current at the same time as the potentials and to divide the drive current into the potential measurements before image reconstruction.

Thus, the required reduction in system noise is achieved by, inter alia, collecting the profiles of data in parallel instead of in series. Data is collected by first driving electrical current between a pair of electrodes and then recording the resulting voltages between all other adjacent pairs of electrodes. This set of voltages is referred to as a profile of measurements. By recording all the voltages in one profile simultaneously each measurement can be allowed to take longer and hence can be made to a higher accuracy. For a system with sixteen electrodes the improvement to be expected by collecting profiles of measurements in parallel rather than in series is $\sqrt{13}$ (11.1 dB). Noise reduction is also achieved by the use of Digital Signal Processing (DSP) technology to carry out all the signal demodulation digitally. A matched filter has been implemented using one DSP system for every four input signals; four DSP systems are used for a sixteen-electrode system. Matched filters have previously been implemented in analogue electronics but the analogue multipliers involved are noisy devices and so the full benefit of the matched filter technique has not been achieved. By using a DSP system the measured noise performance is 20 dB better than the earlier serial data collection system. The image reconstruction algorithm may be a non-iterative back-projection, or an iterative algorithm.

One application or adaptation of the invention is in the measurement of blood flow to organs such as the heart, lungs and brain.

The electrical resistivity of blood is approximately 1.6 Ohm meters. It varies in a well described manner with the haematocrit of the blood. If saline (0.9% solution) which has a much lower resistivity is introduced into the blood then the resistivity of the mixture will be less than that of the blood alone. For example, if 10 ml of saline of resistivity 0.4 Ohm meters is introduced into a person with a blood volume of 5000 ml and resistivity 1.6 Ohm meters then the resistivity of the mixture will fall by about 0.5%. If the time course of this change following an injection of saline into the venous system is measured then the blood flow to that organ can be calculated (Chinard F. P., Enns T. and Nolan M. Circulation Research. Vol X 473–491, 1962). The technique has been used to calculate cardiac output by injecting saline and then measuring the resulting resistivity change in an artery.

In the application or adaptation of the invention for this purpose, however, real-time impedance tomographical imaging will enable measurements to be made non-invasively.

The noise level from the real-time impedance imaging system is sufficiently low to allow changes of 0.5% to be observed relatively easily, and this gives rise to the possibility of obtaining accurate measurements of blood flow by impedance angiography.

Another application is to observe the normal variations in lung resistance during the respiratory and cardiac cycles. As air enters the lungs during respiration there is a proportional increase in tissue resistivity. By monitoring these changes in real-time it is possible for a clinician to extract data relevant to respiratory performance. There are also changes in lung resistivity during the cardiac cycle as the volume of blood perfusing lung tissue changes. These changes are small (typically 2%) but can be observed using the low noise capability of the system and so used to monitor conditions such as plumonary embolism.

The noise levels measured from the method and apparatus in accordance with the invention are surprisingly low and are now limited only by thermal noise.

BRIEF DESCRIPTION OF THE DRAWINGS

The invention is illustrated in greater detail, by way of example, with reference to the accompanying drawings, in which.

DESCRIPTION OF THE PREFERRED EMBODIMENT

Figure 1:
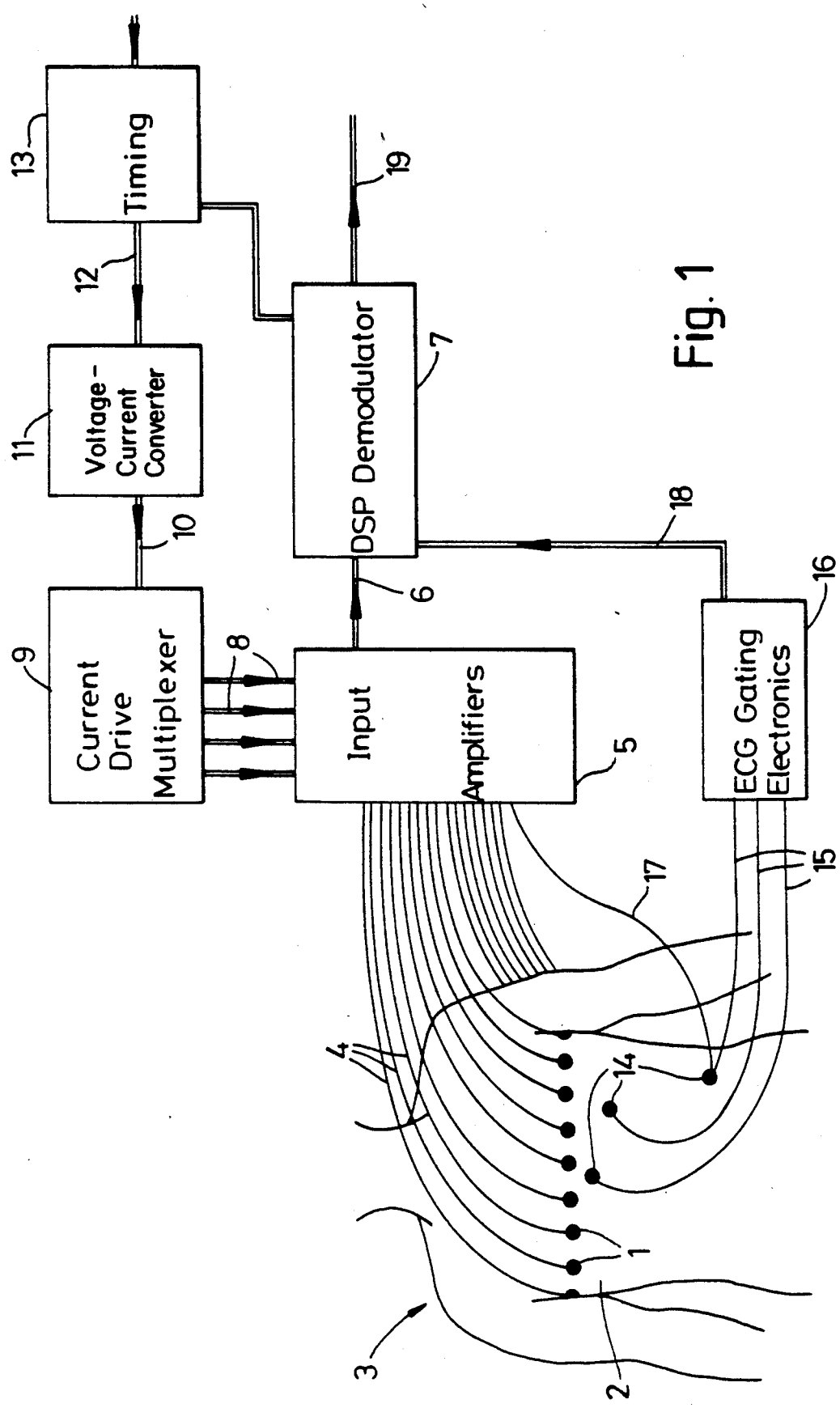
FIG. 1 shows a data acquisiton system for the method and apparatus of the invention.
Figure 2:
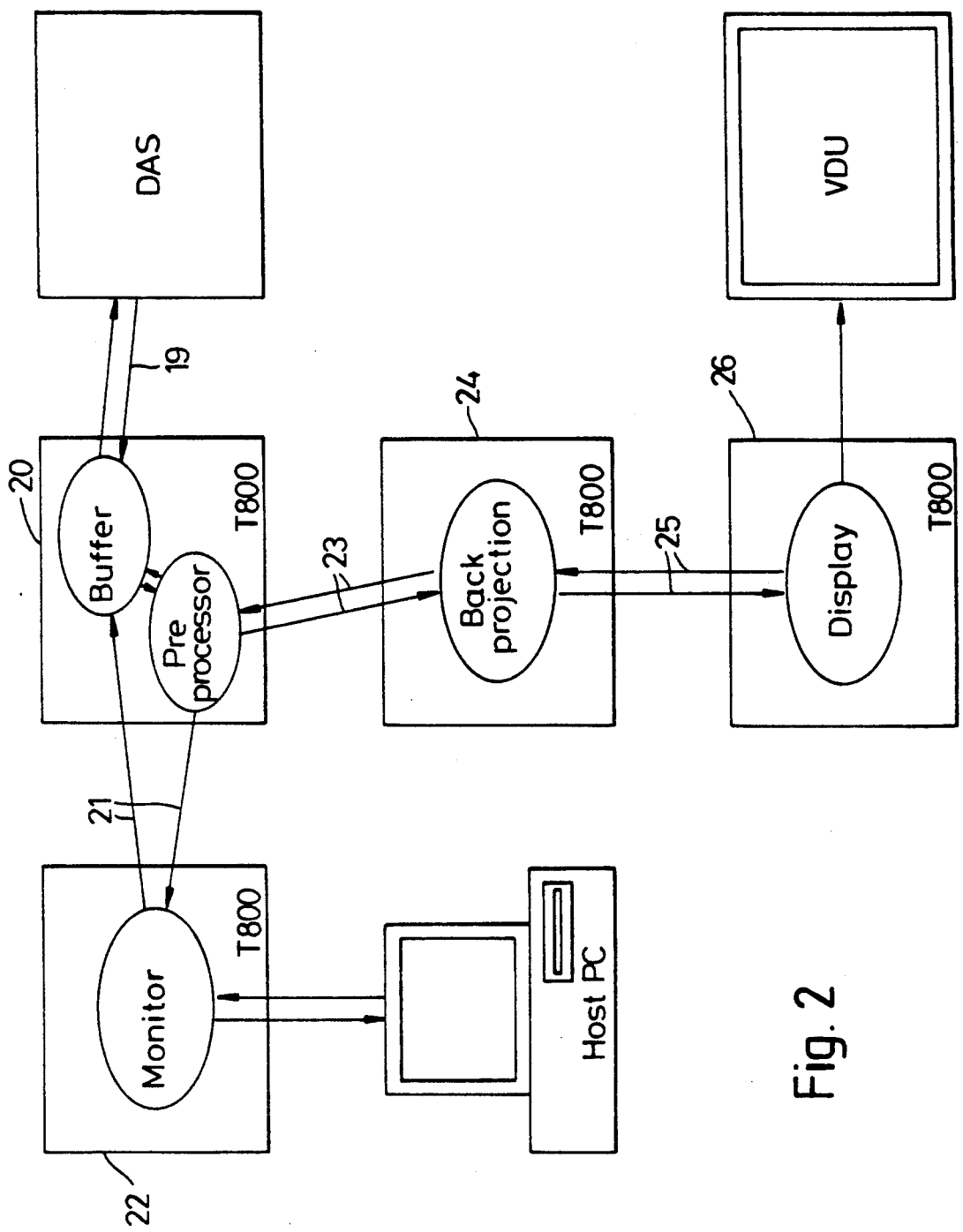
FIG. 2 is a block diagram of an image reconstruction processor.

As indicated in FIG. 1, a plurality of surface contact electrodes 1 are arranged to circumscribe the thorax 2 of a body 3 to be investigated, each electrode 1 being connected by a lead 4 to a plurality of input amplifiers 5, an output 6 of which is to a DSP demodulator 7 incorporating in fact sixteen parallel demodulators. Power input to the input amplifiers 5 is by leads 8 from a current drive multiplexer 9, in turn supplied by lead 10 from a voltage current converter 11, in turn connected by lead 12 to a timing device 13 for the whole system, the elements 1 and 4 to constituting a data acquisition system (DAS) represented by box DAS in FIG. 2. The drive current is measured by the current drive multiplexer.

Also indicated in FIG. 1 are three additional electrodes 14, all of which are connected by leads 15 to an ECG gating electronics system 16 and the third of which is connected by an additional lead 17 to the input amplifier 5, although an ECG is, not essential for monitoring spikes, representing heart beats. This data is transmitted via a lead 18 to the DSP demodulator 7.

An output 19 from the demodulator 7 is to a control transputer 20 connected by lead 21 to a pre-processing and error checking/data laundering transputer 22, a lead 23 to an image construction transputer 24, and by a lead 25 to a display transputer 26, at which data can be captured for subsequent analysis and/or processing, and in accordance with the characterising features of the invention, the voltage differences at an adjacent pair of electrodes 1 is measured simulataneously, this voltage measurement is then demodulated by digital correlation and at the same time, the drive current is measured and divided into voltage measurements before image reconstruction at the transputer 24. The term "transputer" is used in this description to denote any computing machine using parallel processing, capable of the performance necessary to handle the data at a sufficient rate.

As disclosed in U.S. Pat. No. 4,617,939, an image points S representing a point within a region enclosed by a circular boundary has cartesian coordinates x,y relative to an origin at the current dipole. For a uniform medium, an equipotential line is given by the equation $$\left(\frac{x}{x^2 + y^2}\right) = C$$

C being constant. This equipotential line intersects the boundary, and this a boundary potential value v can be assigned to the image point at x,y.

The images which are formed according to the preferred embodiment of this invention use an algorithm implemented as a single matrix multiplication of the measured data set with a matrix of weights.

The weight values which can be used are well known in the art, and can also be found with reference to U.S. Pat. No. 4,617,939 at col. 6 lines 56 through col. 7, line 13. From that reference it is seen that a back projection image is produced using all image points within the boundary. For 16 electrodes there would be 16 such back projection images which are added together in a weighted manner. For each back projection the value of the back projection image at the point x,y is multiplied be a weighting term $$\left(\frac{y}{x^2 + y^2} - \frac{1}{2R}\right)\left(1 - \frac{r^2}{R^2}\right)$$

(Equation 4a of U.S. Pat. No. 4,617,939)

if uniform sensitivity to spaced objects is required, or by $$\left(\frac{y}{x^2 + y^2}\right) - \frac{1}{2R}$$

(Equation 4b of U.S. Pat. No. 4,617,939)

if uniform sensitivity to a distributed change in resistance is required. In these equations, R is the radius of the circular region, r is the radial position of S.

I claim:

1. A method of real time imaging using electrical impedance tomography, comprising:
   a) arranging a plurality of pairs of surface electrodes at spaced apart locations around a body to be investigated;
   b) applying constant current drive to selected electrodes;
   c) measuring the resulting potentials between adjacent pairs of other electrodes; and
   d) forming images using an algorithm implemented as a single matrix multiplication of the measured data set with a matrix of weights, whereby the measurement noise is minimised by:
      (i) measuring potentials between adjacent pairs of said other electrodes simultaneously;

(ii) de-modulating the potential measurement by digital signal processing, and (iii) measuring the drive current at the same time as the potentials, and dividing the drive current into potential measurements before image reconstruction.

2. A method as claimed in claim 1, wherein the algorithm is a non-iterative, back-projection algorithm.

3. Apparatus for carrying out the method of claim 1, comprising:

a) a plurality of pairs of contact electrodes;

b) means to apply constant current drive to selective electrodes;

c) means to measure the resulting potentials between adjacent pairs of other electrodes;

d) means to form images using an algorithm implemented as a single matrix multiplication of the measured data set with a matrix of weights wherein there is further provided:

(i) means to measure the potential between adjacent pairs of said other electrodes simultaneously;

(ii) digital signal processing means to demodulate the potential measurement; and (iii) means to measure the drive current at the same time as the potentials and to divide the drive current into the potential measurements before image reconstruction.

4. Apparatus as claimed in claim 3, wherein the means to measure the potentials between adjacent pairs of said other electrodes simultaneously comprises a plurality of computing machines using parallel processing.

5. Apparatus as claimed in claim 4, wherein the computing machines using parallel processing are a control transputer connected to a pre-processing and error checking transputer, in turn connected to an image construction transputer, which in turn is connected to a display transputer.

6. Apparatus as claimed in any one of claims 3 to 5, wherein the means to measure the drive current comprises a current drive multiplexer.

* * * * *